United States Patent
Wenzel et al.

(10) Patent No.: US 10,438,345 B2
(45) Date of Patent: Oct. 8, 2019

(54) IMPROVING SYMMETRY IN BRAIN SCANS

(71) Applicant: KONINKLIJKE PHILIPS N.V., Eindhoven (NL)

(72) Inventors: Fabian Wenzel, Eindhoven (NL); Elizabeth Anne Moore, Eindhoven (NL); Thomas Heiko Stehle, Eindhoven (NL); Astrid Ruth Franz, Eindhoven (NL); Carsten Meyer, Eindhoven (NL)

(73) Assignee: Koninklijke Philips N.V. (NL)

( * ) Notice: Subject to any disclaimer, the term of this patent is extended or adjusted under 35 U.S.C. 154(b) by 95 days.

(21) Appl. No.: 14/780,247

(22) PCT Filed: Mar. 17, 2014

(86) PCT No.: PCT/IB2014/059878
§ 371 (c)(1),
(2) Date: Sep. 25, 2015

(87) PCT Pub. No.: WO2014/155231
PCT Pub. Date: Oct. 2, 2014

(65) Prior Publication Data
US 2016/0042524 A1 Feb. 11, 2016

Related U.S. Application Data

(60) Provisional application No. 61/806,036, filed on Mar. 28, 2013.

(51) Int. Cl.
*G06T 7/00* (2017.01)
*G06T 3/00* (2006.01)
(Continued)

(52) U.S. Cl.
CPC ............ *G06T 7/0012* (2013.01); *A61B 6/501* (2013.01); *G06T 3/0093* (2013.01); *G06T 7/10* (2017.01); *G06T 2207/30016* (2013.01)

(58) Field of Classification Search
CPC ................. G06T 19/20; G06T 2210/56; G06T 2219/2021; G06T 2207/30016;
(Continued)

(56) References Cited

U.S. PATENT DOCUMENTS

| 4,851,779 A * | 7/1989 | DeMeester .......... G01R 33/561 324/312 |
| 6,907,280 B2 * | 6/2005 | Becerra ................. A61B 5/055 424/9.2 |

(Continued)

FOREIGN PATENT DOCUMENTS

WO 2012093353 A1 12/2012

OTHER PUBLICATIONS

R R Martin et al: "Tools for Asymmetry Rectification in Shape Design",Journal of Systems Engineering, Jan. 1, 1996 (Jan. 1, 1996), pp. 98-112.
(Continued)

*Primary Examiner* — Aklilu K Woldemariam

(57) ABSTRACT

A symmetric model representing anatomical structures of the brain is adapted to a brain scan image with a transform. First and second points provided on first and second hemispheres of the brain image and a patient-specific symmetric anatomical model of the brain is computed based on the transformation.

15 Claims, 7 Drawing Sheets

(51) Int. Cl.
*A61B 6/00* (2006.01)
*G06T 7/10* (2017.01)

(58) Field of Classification Search
CPC ....... G06T 3/0093; G06T 7/0012; G06T 7/10; G06T 2207/10088; G06T 2207/10072; G06T 7/32; G06T 7/73; G06T 7/0014; G06T 2207/10081; G06T 7/11; G06T 7/68; G06T 2207/10104; A61B 6/501; A61B 5/0068; A61B 6/037; A61B 6/4258; A61B 6/507; A61B 6/12; A61B 2034/2051; A61B 34/10; A61B 90/37; A61B 2034/107; A61B 5/06; A61B 6/506; A61B 6/5247; A61B 5/0042; A61B 5/055; A61B 5/168; A61B 5/4064; A61B 5/4824; A61B 5/7239; A61B 5/4094; A61B 5/726; A61B 5/7267; A61B 2576/026; A61N 5/1031; A61N 5/1084; G01R 33/561; G01R 33/56545; G06K 9/3216
USPC ......... 382/128; 324/307, 312, 318; 342/309; 600/407, 425, 428; 345/629
See application file for complete search history.

(56) References Cited

U.S. PATENT DOCUMENTS

| | | | | |
|---|---|---|---|---|
| 8,041,088 | B2 * | 10/2011 | Mallya | A61B 6/032 |
| | | | | 382/128 |
| 8,160,676 | B2 * | 4/2012 | Gielen | A61B 5/06 |
| | | | | 382/128 |
| 9,123,101 | B2 * | 9/2015 | Thiele | G06T 7/68 |
| 9,165,360 | B1 * | 10/2015 | Bates | G06T 7/0014 |
| 2004/0066959 | A1 * | 4/2004 | Pike | G06T 5/003 |
| | | | | 382/128 |
| 2005/0079636 | A1 * | 4/2005 | White | A61B 5/16 |
| | | | | 436/518 |
| 2005/0283070 | A1 * | 12/2005 | Imielinska | A61B 6/032 |
| | | | | 600/425 |
| 2006/0058683 | A1 * | 3/2006 | Chance | A61B 5/0059 |
| | | | | 600/476 |
| 2007/0161886 | A1 | 7/2007 | Rainer et al. | |
| 2008/0021502 | A1 * | 1/2008 | Imielinska | A61B 6/032 |
| | | | | 607/1 |
| 2008/0123922 | A1 * | 5/2008 | Gielen | A61B 5/06 |
| | | | | 382/131 |
| 2008/0292194 | A1 * | 11/2008 | Schmidt | G06T 7/0012 |
| | | | | 382/217 |
| 2010/0021378 | A1 * | 1/2010 | Rousso | A61B 5/411 |
| | | | | 424/1.11 |
| 2010/0066760 | A1 | 3/2010 | Mitra et al. | |
| 2010/0259263 | A1 * | 10/2010 | Holland | A61B 5/055 |
| | | | | 324/310 |
| 2010/0303328 | A1 * | 12/2010 | Ciofolo | G06T 7/12 |
| | | | | 382/131 |
| 2011/0116702 | A1 * | 5/2011 | Bredno | G06T 7/68 |
| | | | | 382/131 |
| 2012/0184840 | A1 * | 7/2012 | Najarian | G06K 9/629 |
| | | | | 600/408 |
| 2013/0289395 | A1 * | 10/2013 | Thiele | G06T 7/68 |
| | | | | 600/425 |

OTHER PUBLICATIONS

Zabrodsky H et al: "Using Bilateral Symmetry to Improve 3D Reconstruction From Image Sequences",Computer Vision and Image Understanding, Academic Press, US, vol. 6 7, No. 1, Jul. 1, 1997 (Jul. 1, 1997),pp. 48-57.

Fletcher et al, "Quantifying Metabolic Asymmetry Modulo Structure in Alzheimers Disease", Jul. 2, 2007 (Jul. 2, 2007), Information Processing in Medical Imaging; Lecture Notes in Computer Science; Springer Berlin Heidelberg, Berlin, Heidelberg, pp. 446-457.

Hugdahl, "Symmetry and Asymmetry in the Human Brain" Euopean Review, vol. 13, Supp. No. 2., p. 119-133 (2005).

Merhof et, al, "Analysis of Asymmetries in ICTAL and Inter-ICTAL Spect Images for the Localization of Epileptic Foci" 2010 IEEE Nuclear Science Symposium, Oct. 30, 2010.

* cited by examiner

IMPROVING SYMMETRY IN BRAIN SCANS

CROSS-REFERENCE TO PRIOR APPLICATIONS

This application is the U.S. National Phase application under 35 U.S.C. § 371 of International Application No. PCT/IB2014/059878, filed on Mar. 17, 2014, which claims the benefit of U.S. Patent Application No. 61/806,036, filed on Mar. 28, 2013. These applications are hereby incorporated by reference herein.

BACKGROUND

In neurology, many applications of quantitative imaging relate information at corresponding positions in the left and right hemisphere of the brain. Region of Interest (ROI) based comparisons between left and right hemisphere of the brain can play an important role across many imaging modalities and clinical questions. Generally, these applications take advantage of corresponding portions of the left and right hemispheres to, for example, compare the anatomy and make an appropriate diagnosis. These applications reflect locations about the mid-sagittal plane, which divides the left and right hemispheres. Using image analysis techniques, the brain scan is oriented such that the mid-sagittal plane is mapped to a pre-defined position P on the x-axis. Subsequently, corresponding points in the left and right hemisphere are identified via reflecting the x-axis component of a point at P. These applications typically assume that the brain is symmetric with respect to the mid-sagittal plane. However, this assumption is not always true. Rather, regional anatomical asymmetry typically exists across individuals, degrading the power of approaches that assume brain symmetry (mirroring, asymmetry measures). Furthermore, an individual brain is typically not perfectly symmetric but rather, contains normal and abnormal asymmetries. This fact is well known under the term "brain lateralization". Whereas normal causes of asymmetry include lateralization of brain functionality or just individual cortex anatomy, abnormal asymmetry might also be caused by tumors, stroke, or neurodegenerative diseases.

Standard image analysis techniques attempt to limit individual asymmetry in the brain by deforming the image via a symmetric template based on image registration, commonly denoted as stereo tactical normalization. However, many registration techniques limit the types of deformation that may be completed via parameterization (e.g. b-splines or linear transformations) and are not able to eliminate a brain's asymmetry as the possible deformations do not match the anatomy of a brain. There may be a need for a system that permits the use of quantitative imaging while accounting for variable asymmetries in the brain.

SUMMARY

A system and method including adapting a symmetric model representing anatomical structures of the brain, the model corresponding to a brain scan image, transforming first and second points provided on first and second hemispheres of the brain and computing, based on the transformation, a patient-specific symmetric anatomical model of the brain.

BRIEF DESCRIPTION OF THE DRAWINGS

Several exemplary embodiments of the invention will be described in the following by way of example and with reference to the accompanying drawings in which.

DETAILED DESCRIPTION

The exemplary embodiments may be further understood with reference to the following description and appended drawings. The exemplary embodiments can provide a system and method for locally detecting anatomical asymmetry in brain scans and considering this information for improving following analyses (mirroring, asymmetry measures). The system and method according to the exemplary embodiments can also reduce anatomical asymmetries in a brain scan via model-based segmentation thereof. The model-based segmentation can allow for the removal of asymmetry on a desired granularity of the brain, including any number of sub-cortical structures or, in another embodiment, of the entire cortex, as will be described in greater detail later on. Furthermore, the exemplary segmentation can enable the computation of improved symmetric patient brain images in a manner selected to preserve much of the patient's residual, symmetric brain anatomy.

Figure 1:
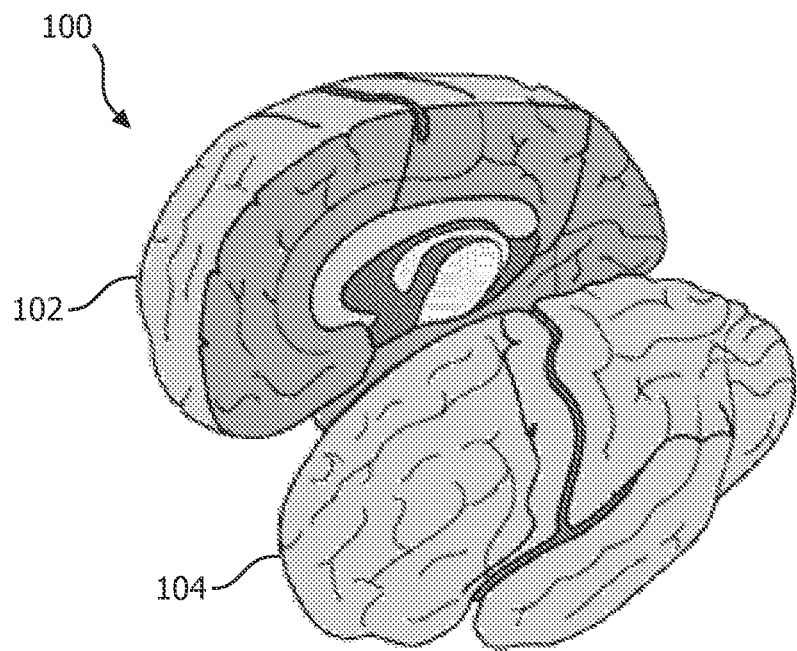
FIG. 1 depicts a perspective view of a symmetric brain model.
Figure 2:
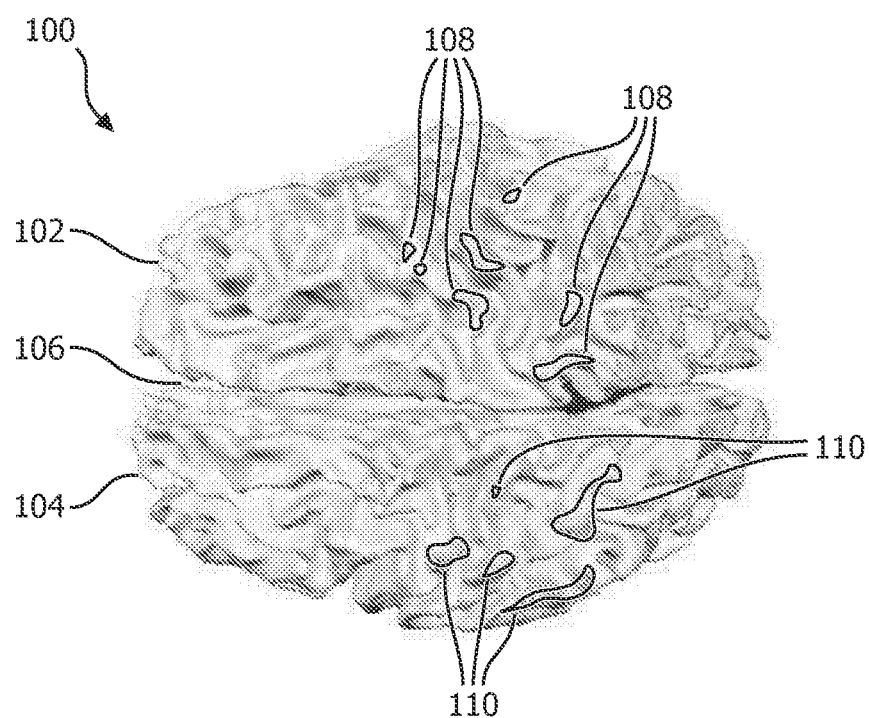
FIG. 2 depicts a perspective view of a brain model having asymmetrical portions therein.

FIGS. 1-2 depict an illustration of a brain 100. Prior art imaging techniques assume a perfect symmetry of right and left hemispheres 102, 104 along the longitudinal fissure 106. However, it is no such perfect symmetry exists. Rather, border areas 108, 110 show asymmetries along both the longitudinal fissure 106 as well as lateral cortical areas.

Figure 3:
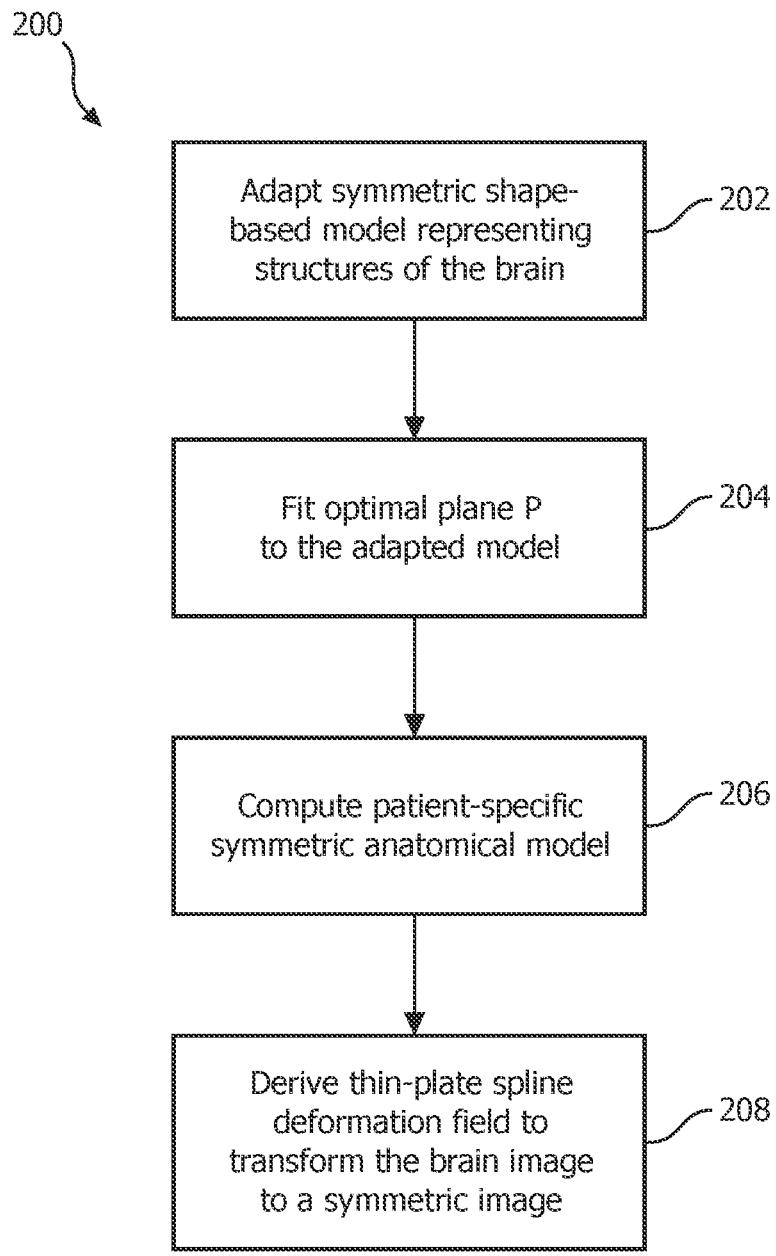
FIG. 3 depicts a flow diagram of a first exemplary method.
Figure 4:
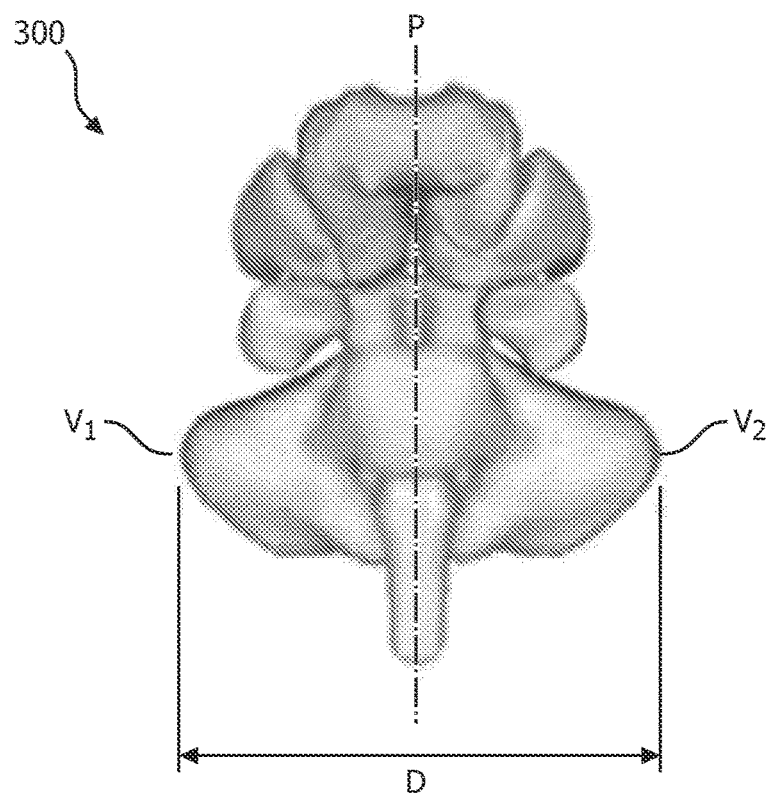
FIG. 4 depicts a first perspective view of a symmetrical model of sub-cortical structures of a brain formed in accordance with an exemplary method.
Figure 5:
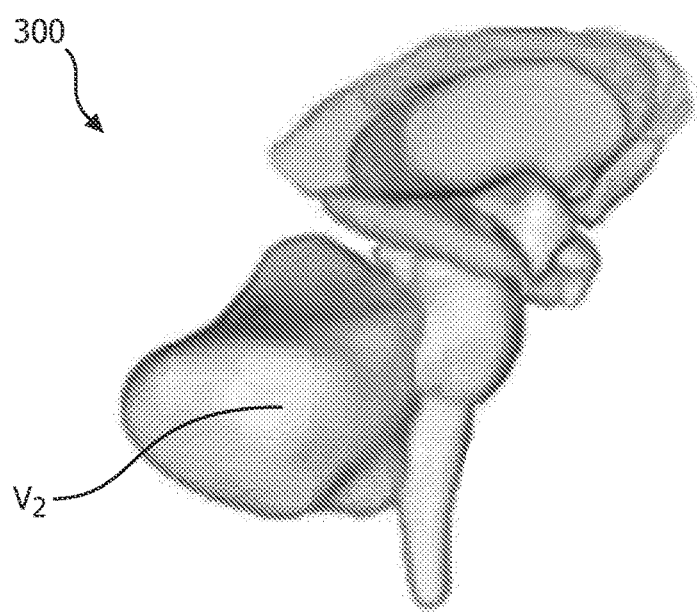
FIG. 5 depicts a second perspective view of the symmetrical model of FIG. 4.
Figure 6:
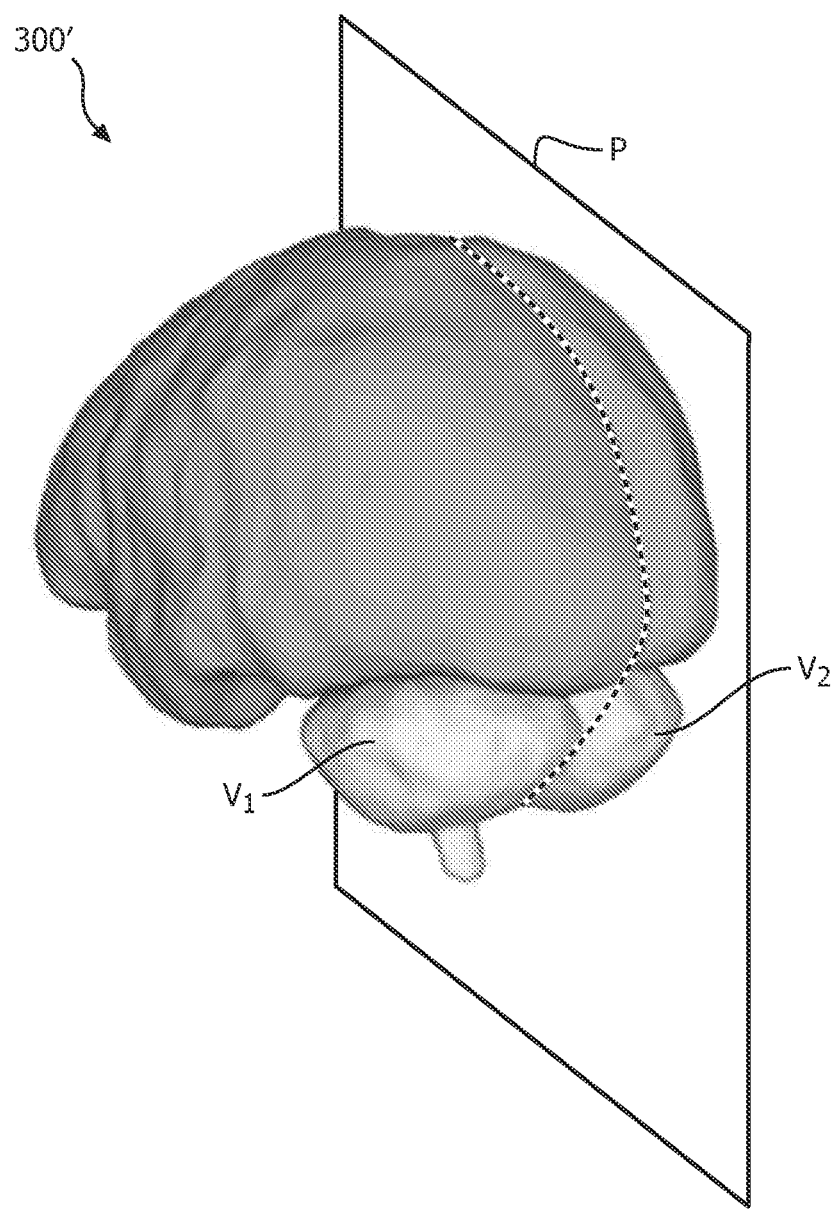
FIG. 6 depicts a perspective view of a symmetrical model of right and left hemispheres of a brain formed in accordance with an exemplary method.

FIG. 3 depicts an exemplary method 200 according to a first exemplary embodiment. In a first exemplary step 202, an adaptation of an artificial symmetric shape-based model 300 is formed, the shape-based model 300 representing the surfaces of anatomical sub-structures in the brain. The model 300, as shown in FIGS. 4-6, is based on image analysis and is an adapted mesh comprising a triangle structure T and a set of adapted vertices $V_1$, $V_2$. It is noted that although the exemplary embodiment is described with respect to vertices of the adapted model, any other point or points of interest of the model may be employed for the transformation without deviating from the scope of the disclosure. The model 300 may be formed based on a current image scan of the brain or, in another embodiment, may use one or more previous brain scan images (not shown) to aid in construction thereof. The model 300 of FIGS. 4-5 displays only sub-cortical brain structures while the model 300' of FIG. 6 depicts right and left brain hemispheres. It is noted that although only one pair of corresponding vertices $V_1$, $V_2$ are depicted in the model 300, 300', any plurality of vertices may be employed without deviating from the scope of the description. In the next step 204, an optimal symmetrical plane P is fitted to the model 300, the plane P being positioned such that a sum of squared distances between the vertices $V_1$, $V_2$ is minimized. It is noted, however, that the use of a minimized squared distance for positioning of the plane is exemplary only and that any other method for placement of the plane may be employed without deviating from the scope of the disclosure. In an exemplary embodiment, a position of the plane P is determined by minimizing this distance between any pluralities of vertices. As a three-dimensional plane has three degrees of freedom, a minimum of three corresponding vertices are needed in order to define a plane minimizing the distance between of corresponding vertices. However, generally, a surface model of the brain may include several hundreds of corresponding vertex pairs. In this case, any or all of these vertices may be used for defining a position of the optimal plane P. Alternatively, a (weighted) subset of vertices may be chosen by different criteria. One example criterion is that the spatial distribution of corresponding vertices is distributed equally across space perpendicular to the plane to be fit, but other constellations which focus on a set of dedicated anatomical structures of interest are also possible. It should be noted that the objective of a symmetrical mid-sagittal plane P is describing one embodiment enhancing improved mirroring functionality. Corresponding locations in a symmetric brain model can also be derived in areas that are not related to the mid-sagittal plane. For example, a position in one area of interest in one hemisphere might be linked to a matching area in the other hemisphere by finding local parametrizations of the position in one hemisphere, based on the adapted anatomical model, and transforming the position to the other hemisphere by computing the local parametrization of the position in the adapted structure of the other hemisphere. It is further noted that the system and method disclosed herein may be used for the correction of images in any of two-dimensions (e.g., for correcting a single slice of a brain scan image), three-dimensions and four-dimensions (e.g., a time series of brain scans for PET/MR devices).

In a next exemplary step 206, a patient-specific symmetric anatomical model (not shown) can be computed based on the results of steps 202, 204. Specifically, the patient-specific symmetric anatomical model (not shown) is formed with adjusted anatomical sub-structures having vertices $V_1'$, $V_2'$, each of which is separated from a mid-plane (not shown) thereof by a distance of D/2. The adjusted symmetric anatomical model (not shown) thus includes any plurality of corresponding pairs of vertices $V_1'$, $V_2'$, all of which are symmetric about the mid-plane (not shown). In a next step 208, a thin-plate spline deformation field is derived to transform the complete artificial model to a symmetric model based on the relationship between V and V'. As those skilled in the art will understand, the thin-plate spline determines a two-dimensional displacement of x and y coordinates of the original two-dimensional brain scan as a function of the deviations of vertices $V_1'$, $V_2'$ relative to the vertices $V_1$, $V_2$ in the three-dimensional patient-specific symmetric model. The exemplary symmetry removal according to the exemplary embodiments may be optionally switched on and off by a user via a control switch, thus permitting the user to examine the original and symmetry adjusted models as well as the original and adjusted brain scans as necessary.

Figure 7:
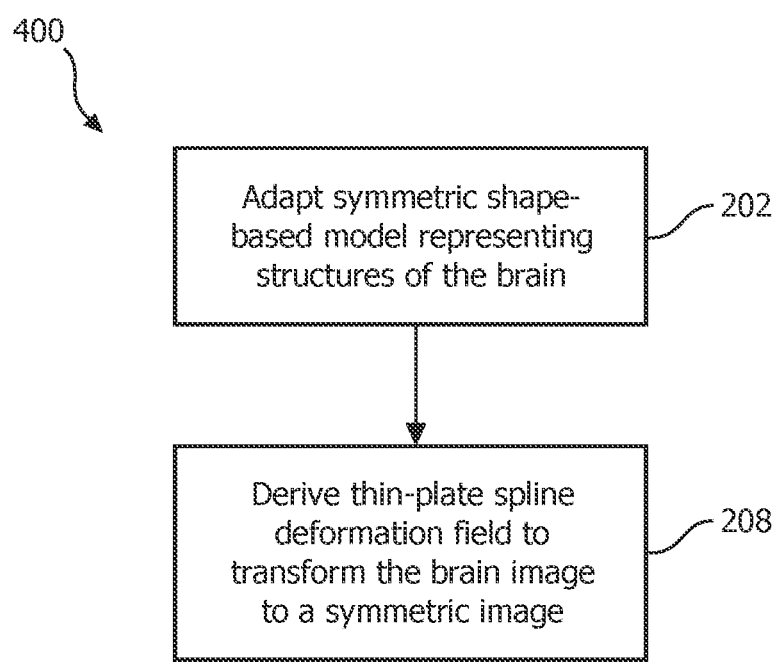
FIG. 7 depicts a flow diagram of a second exemplary method.

FIG. 7 depicts a method 400 according to another exemplary embodiment of the invention. Specifically, the method 400 includes the first step 202 which forms an adapted symmetric shape-based model representing surface of anatomical sub-structures in the brain. The method 400 skips steps 204, 206 and instead uses locations of vertices of the model 300 to directly transform an asymmetric brain scan (not shown) to the original symmetric unadapted model space. As those skilled in the art will understand, this method does not preserve residual patient anatomy in the brain.

Figure 8:
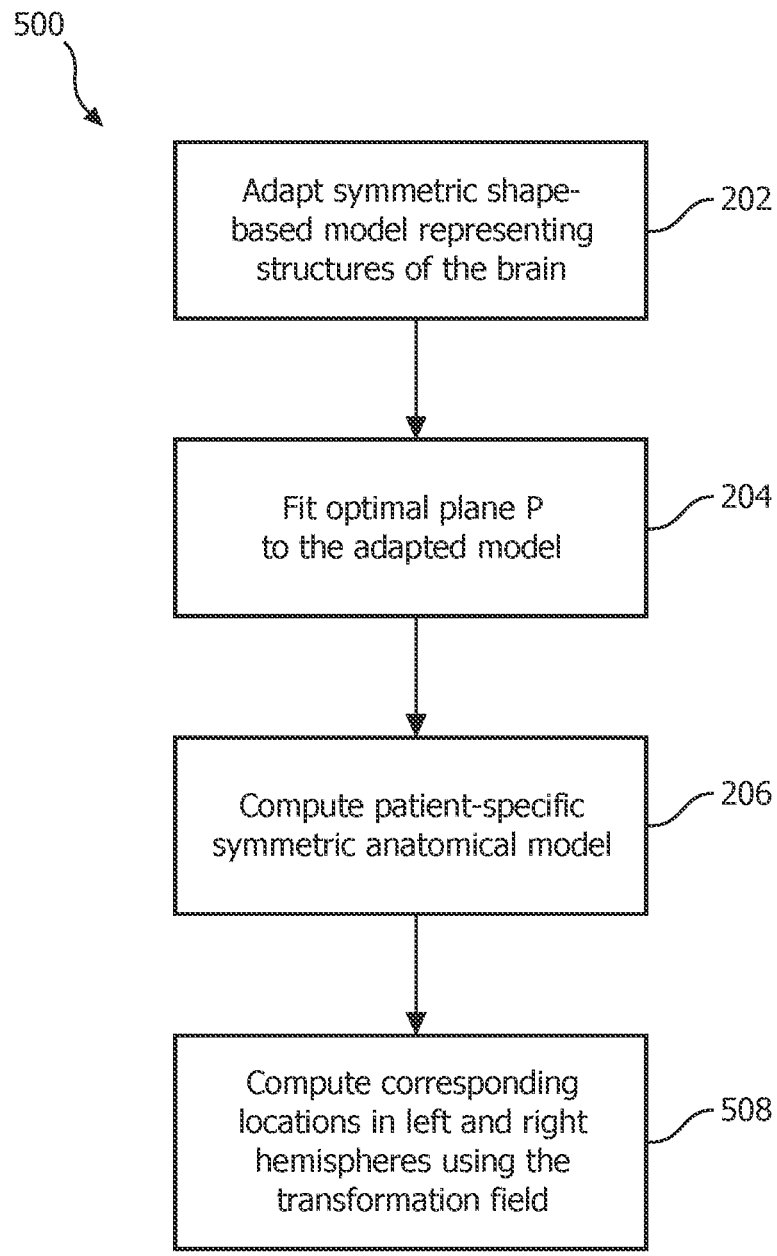
FIG. 8 depicts a flow diagram of a third exemplary method.

FIG. 8 depicts a method 500 according to another exemplary embodiment of the invention. Specifically, the method 500 incorporates steps 202 through 206 of the method 200 and omits step 208. Instead, after computing the patient-specific symmetric anatomical model in step 206, the method 500 proceeds to step 508 where the transformation field is used to compute corresponding locations in the left and right hemispheres of the original brain scan. A radiologist or other user may then reference this data to determine which portions of the original, asymmetric brain scan correlate with one another. This method provides the possibility of inspecting the original unprocessed slices of the brain while still benefiting from improved symmetric ROI quantification, as those skilled in the art will understand.

The exemplary methods disclosed herein permit the interactive analysis of a brain model by removing asymmetries therein. That is, the resultant model/image according to the invention permits the analysis of only a single "hemisphere" of the brain, the hemisphere being defined by a plane P which may or may not coincide with a longitudinal fissure of the brain. Thus, a physician or other user may analyze the selected hemisphere to make an analysis of the brain in applications ranging from an all-purpose "mirror ROI" tool to asymmetry indices in epilepsy and fMRI lateralization analysis. It is noted, however, that embodiments of the invention are generally directed toward normal asymmetries in the brain and not intended for the analysis of abnormal asymmetries which may occur in only one hemisphere (e.g., strokes, lesions, oncology, etc.).

Figure 9:
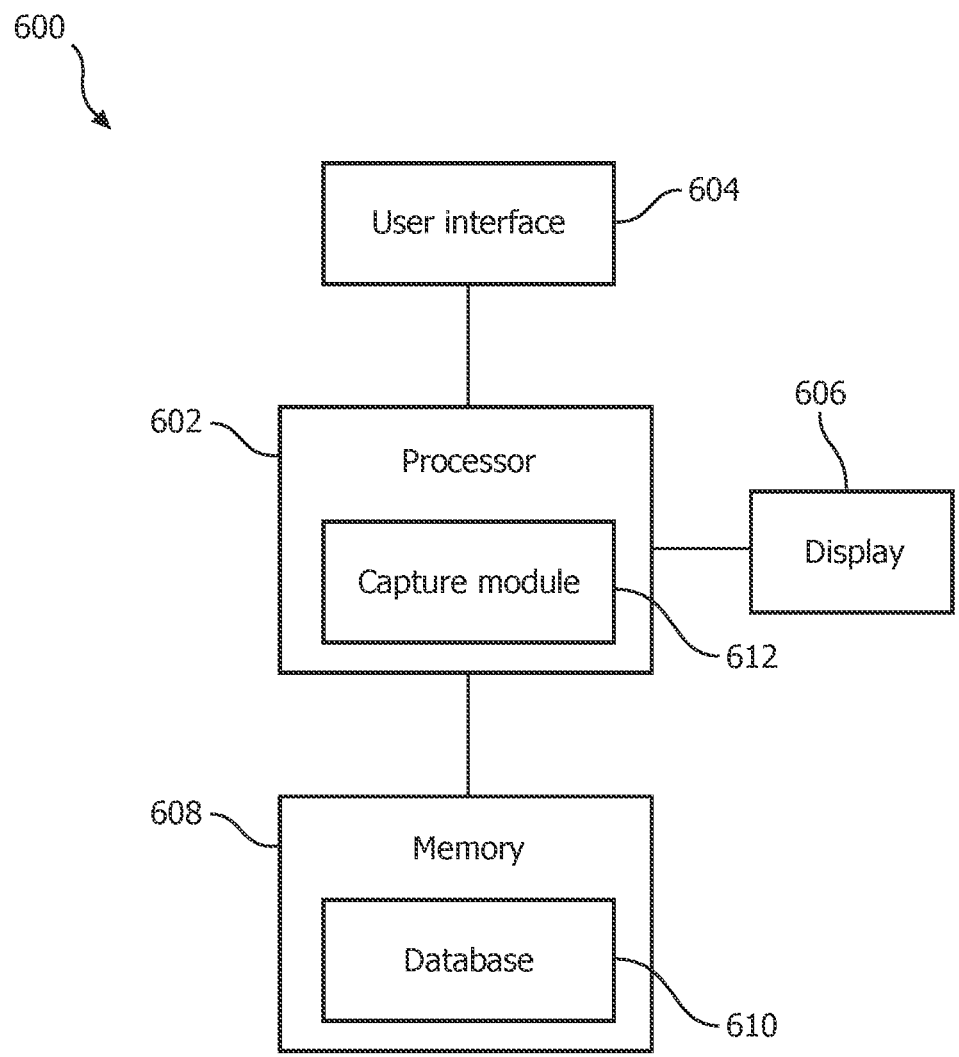
FIG. 9 shows a schematic drawing of a system according to an exemplary embodiment.

As shown in FIG. 9, an exemplary system 600 according to an exemplary embodiment of the present disclosure generates data corresponding to symmetry of a brain scan image, the data including one or both of an adjusted brain scan image and data indicating corresponding locations of symmetry of the brain, as described in greater detail earlier. The system 600 comprises a processor 602, a user interface 604, a display 606 and a memory 608. The processor 602 analyzes the brain scan image, which may be stored in the memory 608, and determines an adjusted symmetrical relationship therein, as described in greater detail above with respect to the methods 200, 400, 500. A database 610 of the memory 608 may include additional data with regard to the patient (e.g., age, weight, height, medical history, etc.) and/or the brain scan image (e.g., date and time of image capture, etc.). The database 118 may also store for example, annotations (i.e., mark-ups on the brain scan image) relating to the patient medical history and other findings of relevance to a neurodegenerative condition of the patient. The processor 602 further includes a capture module 612, which captures and stores the transformed and/or adjusted brain scan to the database 610 whenever a new annotation is created on the image by a user via input devices such as, for example, a keyboard, mouse, and/or touch display on the display 606.

The system and method according to exemplary embodiments of the invention may be incorporated as a feature in any neurological image analysis application on different medical devices (e.g., consoles, workstations, PACS applications, etc.), as those skilled in the art will understand. Furthermore, although the invention has been described with a model-based segmentation, any other image analysis technique may be used without deviating from the scope of the invention. For example, the image analysis may include atlas- or multi-atlas-registration techniques which allow the identification of corresponding positions of surfaces of anatomical structures in the brain (e.g., if the atlas includes corresponding locations at the boundary or inside anatomical regions in the brain). Other examples include landmark detection techniques which are tailored to identify a set of corresponding locations in the left and right hemisphere directly. It will be appreciated by those skilled in the art that various modifications and alterations of the invention can be made without departing from the broad scope of the appended claims. Some of these have been discussed above and others will be apparent to those skilled in the art.

The invention claimed is:

1. A method for reducing structural anatomical asymmetry in a brain scan image, comprising:
obtaining the brain scan image having asymmetry;
adapting a symmetric shape-based model to the brain scan image, wherein the symmetric shape-based brain model represents surfaces of anatomical sub-structures in the brain as an adaptive mesh including a plurality of corresponding vertex pairs, each corresponding vertex pair including corresponding vertices in first and second hemispheres of the brain, to generate an adapted mesh comprising a set of adapted vertex pairs $V_1$, $V_2$;
fitting a mid-plane to the adapted mesh, the mid-plane being positioned and oriented to minimize a sum of a squared distance between the corresponding first and second hemisphere adapted vertex pairs $V_1$, $V_2$; and
computing a patient-specific symmetric anatomical model of the brain by making the corresponding adapted vertices $V_1$ and $V_2$ of the vertex pairs $V_1$, $V_2$ of the adapted mesh symmetric about the mid-plane to generate the patient-specific symmetric anatomical model of the brain with symmetric vertex pairs $V_1'$ and $V_2'$.

2. The method of claim 1, wherein the fitted mid-plane is offset from a longitudinal fissure of the brain shown in the brain scan image.

3. The method of claim 1, wherein the symmetric model is one of two-dimensional, three-dimensioned and four-dimensional.

4. A system for reducing structural anatomical asymmetry in a brain scan image obtained of a patient, the system comprising:
a processor configured to:
adapt a symmetric shape-based model to a brain scan image, wherein the symmetric shape-based model represents surfaces of anatomical sub-structures in a brain as an adaptive mesh, wherein the symmetric shape-based model comprises a plurality of corresponding vertex pairs;
fit a mid-plane to the adapted symmetric shape-based model, the mid-plane being positioned and oriented to minimize a sum of squared distances between the corresponding vertex pairs of the adapted symmetric shape-based model;
compute a patient-specific symmetric anatomical model of the brain by making the corresponding vertex pairs of the adapted symmetric shape-based model symmetric about the mid-plane.

5. The system of claim 4, wherein the adapted symmetric shape-based model is an adapted symmetric three-dimensional model.

6. The system of claim 4, wherein the mid-plane is offset from a plane housing a longitudinal fissure of the brain.

7. The system of claim 4, wherein the symmetric shape-based model depicts only sub-cordical brain structures.

8. The system of claim 4, wherein the processor is further configured to:
determine a transform between the symmetric shape-based model and the patient-specific anatomical model.

9. The system of claim 8, further including:
a display configured to display at least the brain scan image, the patient-specific symmetric anatomical model, and the brain scan image adjusted in accordance with the patient-specific model.

10. The system of claim 4, wherein the processor is further configured to:
transform the brain scan image to a coordinate system of the symmetric shape-based model to generate a symmetric brain image.

11. A system for reducing structural anatomical asymmetry in a brain scan image of a patient, the system comprising:
a processor configured to:
receive the brain scan image and a symmetric shape-based brain model, the symmetric shape-based brain model representing at least sub-cordical brain structures,
adapt the symmetric shape-based brain model to corresponding brain structures of the brain scan image,
fit a mid-sagittal plane to the adapted shape-based brain model,
based on the adapted shape-based brain model and the first mid-sagittal plane, forming a patient specific brain model,
deriving a transform between the patient specific brain model and the symmetric shape-based brain model,
with the transform, converting the brain scan image to a symmetric brain image; and
a display configured to selectively display the brain scan image and the symmetric brain image;
wherein the symmetric shape-based brain model represents surfaces of anatomical substructures in a brain as an adaptive mesh including a plurality of corresponding vertex pairs, the vertices of each pair being disposed in different hemispheres of the brain, and wherein the processor is further configured to fit the mid-sagittal plane to the adapted shape-based brain model by positioning and orienting the mid-sagittal plane to minimize a sum of square distances between the mid-sagittal plane and the corresponding vertex pairs.

12. The system of claim 11, wherein in the symmetric brain image, corresponding vertex pairs are symmetric about the mid-sagittal plane.

13. The system of claim 11, further including:
a user interface configured to enable a user to toggle back and forth between the brain scan image and the symmetric brain image.

14. The system of claim 11, wherein the processor is further configured to:
use the transform to identify corresponding locations in left and right hemispheres in the brain scan image.

15. The system of claim 11, wherein the symmetric shape-based model depicts only sub-cortical brain structures.

* * * * *